(12) United States Patent  (10) Patent No.: US 8,414,690 B2
Hansen et al.  (45) Date of Patent: Apr. 9, 2013

(54) OFF GAS PURIFICATION

(75) Inventors: Jaron C. Hansen, Springville, UT (US);
Lee D. Hansen, Saratoga Springs, UT (US)

(73) Assignee: Bringham Young University, Provo, UT (US)

(*) Notice: Subject to any disclaimer, the term of this patent is extended or adjusted under 35 U.S.C. 154(b) by 306 days.

(21) Appl. No.: 12/859,546

(22) Filed: Aug. 19, 2010

(65) Prior Publication Data

US 2011/0041689 A1    Feb. 24, 2011

Related U.S. Application Data

(60) Provisional application No. 61/274,870, filed on Aug. 21, 2009.

(51) Int. Cl.
*B01D 53/04* (2006.01)

(52) U.S. Cl.
USPC ............. 95/115; 95/148; 96/146; 96/152

(58) Field of Classification Search ........... 95/114, 95/115, 117, 136, 139, 148; 96/121, 126–128, 96/130, 146, 152, 143
See application file for complete search history.

(56) References Cited

U.S. PATENT DOCUMENTS

| | | | | | |
|---|---|---|---|---|---|
| 2,989,383 | A | * | 6/1961 | Miller | 422/200 |
| 3,734,293 | A | * | 5/1973 | Biskis | 210/185 |
| 3,735,563 | A | * | 5/1973 | Adams | 96/127 |
| 4,133,762 | A | * | 1/1979 | Visceglia et al. | 210/186 |
| 4,237,620 | A | * | 12/1980 | Black | 34/72 |
| 4,343,629 | A | * | 8/1982 | Dinsmore et al. | 95/93 |
| 4,545,428 | A |   | 10/1985 | Onishi et al. | |
| 5,286,282 | A | * | 2/1994 | Goodell et al. | 96/113 |
| 5,298,054 | A | * | 3/1994 | Malik | 95/99 |
| 5,658,369 | A | * | 8/1997 | Kusay | 95/41 |
| 5,861,050 | A | * | 1/1999 | Pittel et al. | 95/115 |
| 6,066,192 | A | * | 5/2000 | Toshinaga et al. | 95/93 |
| 6,638,348 | B2 | * | 10/2003 | Kuriiwa et al. | 96/146 |
| 7,744,677 | B2 | * | 6/2010 | Barclay et al. | 95/114 |
| 2003/0192430 | A1 | * | 10/2003 | Pearlstein et al. | 95/90 |
| 2004/0197253 | A1 |   | 10/2004 | Twigg | |
| 2007/0031302 | A1 |   | 2/2007 | Wittrup et al. | |
| 2008/0209933 | A1 |   | 9/2008 | Kidwell et al. | |

OTHER PUBLICATIONS

U.S. Appl. No. 61/207,533, filed Feb. 13, 2009.
Adsorption by powders & porous solids: principles, methodology and applications. Françoise Rouquerol, Jean Rouquerol and Kenneth Sing. Publisher: San Diego, Calif.: Academic Press, 1999. ISBN: 0125989202.
Gas separation by adsorption processes. Ralph T. Yang. Publisher: Boston: Butterworths, 1987. ISBN: 0409900044; Chapter 1, pp. 1-8; Chapter 2, Sec. 2.1.5, pp. 26; Chapter 6, pp. 201-210.

* cited by examiner

*Primary Examiner* — Frank Lawrence, Jr.
(74) *Attorney, Agent, or Firm* — Workman Nydegger

(57) ABSTRACT

Heat-exchangers and biogas conditioners including a heat exchange member disposed between upper and lower flanges of the apparatus in which at least the heat exchange member is formed of a highly thermally conductive material (e.g., at least 50 W/m–K) such as aluminum or aluminum alloy. A bed of zeolite is loaded within the apparatus so as to be in contact with the heat exchange member. The heat exchange member is shaped and configured so that any given location of the zeolite bed is no more than about 3 inches from the heat exchange member comprising the highly thermally conductive material.

20 Claims, 10 Drawing Sheets

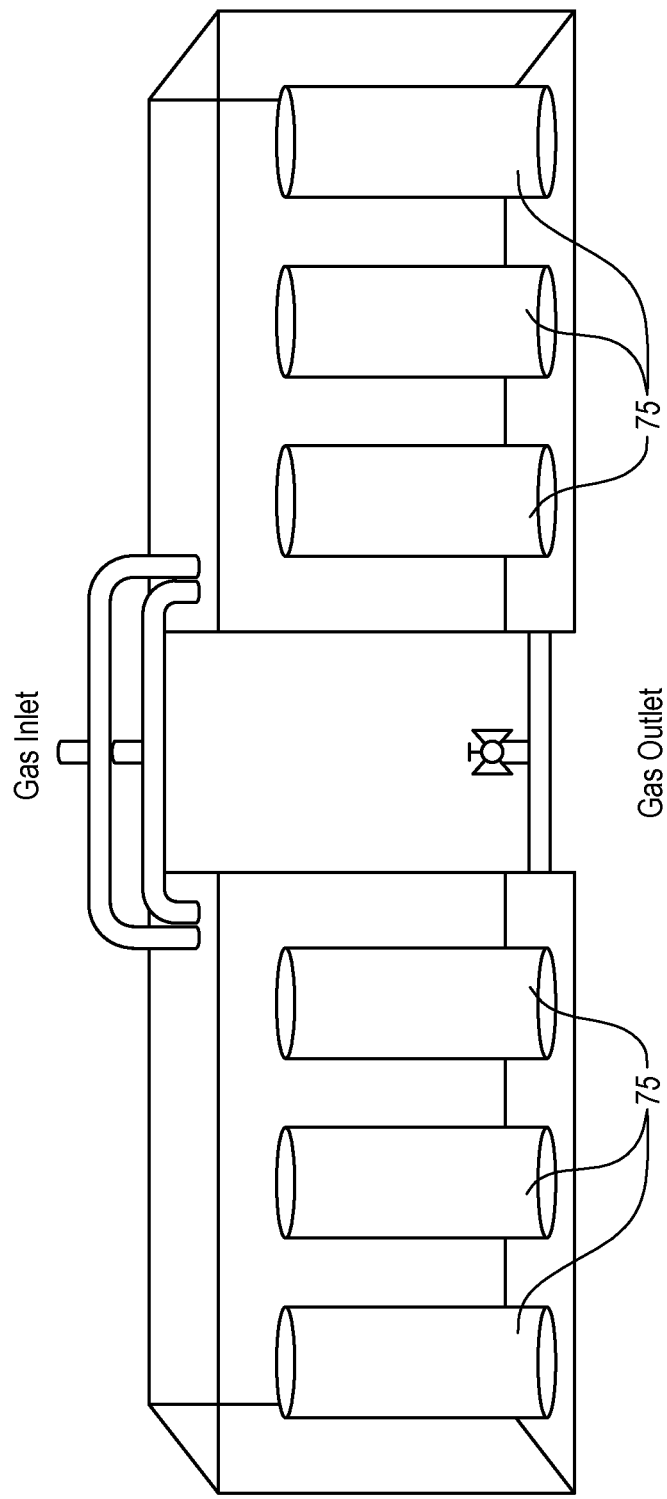

OFF GAS PURIFICATION

CROSS-REFERENCE TO RELATED APPLICATION

This application claims the benefit under 35 U.S.C. §119 of U.S. provisional application Ser. No. 61/274,870, filed Aug. 21, 2009 entitled SPIRAL FIN HEAT EXCHANGER APPARATUS AND SYSTEM FOR HEAT MANAGEMENT. The disclosure of the above application is incorporated herein in its entirety.

BACKGROUND OF THE INVENTION

1. The Field of the Invention

The present invention relates generally to heat management of chemical reactions and relates more specifically to a device, apparatus, and method for the purification of biogas and other sour gas streams. As used herein, the term "biogas" is to be broadly construed so as to include other sour gas streams.

2. The Relevant Technology

Heat management has many applications, including but not limited to the fuel cell industry, production of glass beads, the use of bacteria to make useful products, the production of yogurt, polymerase chain reactions, nanotechnology, and chemical reactions. For example, U.S. Pat. No. 6,881,703 discloses that a specific example of a field in which reactor temperature control is particularly important is in systems for the reforming of hydrocarbon feed streams to generate hydrogen-rich gases for the operation of hydrogen fuel cells. In a chemical reactor, regardless of its configuration or size, two variables that may affect the reaction rate are time and temperature. By controlling the heat transfer, and thus the temperature, the length of time a reaction or process requires for completion can be determined. For this reason, temperature control is a critical reactor design consideration for chemical processes. On an industrial scale, surface area-to-volume ratios may make heat transfer and temperature control difficult. Example processes wherein managing reactor heat is important include, but are not limited to, selective oxidations to make products such as ethylene oxide, phthalic anhydride, maleic anhydride, formaldehyde, acrylonitrile, acrolein, acrylic acid, methacrolein, methacrylic acid, methacrylonitrile, 1,2-dichloroethane, vinyl chloride, methanol synthesis, and Fischer-Tropsh synthesis.

Heat management is also important to purification processes. For example, many people have tried to convert biomass and other carbon-containing materials to methane or other useful products. Recent discoveries suggest that there may be an economical method to convert cellulosic and lignocellulosic materials into biogas, that is, unpure methane and/or hydrogen gas.

Biogas produced by microbial anaerobic digestion in an anaerobic digester has been used as a fuel source, usually for on-site heating or for electricity production. As a consequence of the digestion process, high concentrations of hydrogen sulfide, carbon dioxide, and water are typically observed in the biogas stream. For example, such biogas may include about 75% $CH_4$, about 20% $CO_2$, and significant fractions of $H_2S$ and $H_2O$. Downstream utilization of the methane produced from the digestion process has been hindered by high concentrations of these impurities. For example, use of unpurified biogas to drive engine turbines can quickly lead to corrosion (e.g., pitting) of the turbine or other engine components.

SUMMARY OF THE INVENTION

Provisional Application Ser. No. 61/207,533 filed Feb. 13, 2009 entitled BIOGAS/SOUR GAS CONDITIONING WITH A ZEOLITE BED is herein incorporated by reference in its entirety. The above application discloses a flow reactor and contaminant detection system. Biogas or sour gas is introduced into a flow tube/packed bed at ambient pressures; the output of the flow tube is "T'ed" to allow a fraction of the gas to be directed into a detection cell that allows for measurement of the gases passing into and out of a zeolite bed; porous plugs could be incorporated into the flow tube to provide mechanical support to hold the zeolite bed in place; a series of ports could be located down the length of the flow tube/packed bed that would allow for thermometers, pressure transducers and analyzer probes to be inserted into the flow tube and zeolite bed.

The above application discloses a methodology that could be used in at least one embodiment, in which 1) an appropriate amount of zeolite is sandwiched between porous plugs in the flow tube; 2) the correct amount of zeolite is determined based on the concentration of $H_2S$, $CO_2$, and $H_2O$ that is in the biogas that will be processed; and 3) the concentration levels of these gases could be used in conjunction with the known gas flow rates and trapping capacity of the zeolite to design a system that would allow biogas to be cleaned in approximately 6 to 12 hours. Breakthrough of contaminants following saturation of the zeolite could be determined by sampling the purity of the biogas through the downstream port using one or more detectors. Measurement of the concentration of these gases could take place about every 2 minutes. Zeolite could be regenerated in many different ways.

According to one method, after the zeolite has become saturated with $H_2S$, $CO_2$, $H_2O$, and any other impurities that may be present, the zeolite could be heated to approximately 200° C. by providing heat directly to the zeolite while passing a dry $N_2/O_2$ gas or air stream through the zeolite. The above application discloses that slower flow rates of dry $N_2/O_2$ could require more time for regeneration than do faster flow rates; the purity of the evolved gases could be measured via a downstream sampling port; when $H_2S$, $CO_2$, $H_2O$, and any other impurities that were present are no longer detected, the zeolite is presumed to have been regenerated and to be ready for reuse.

According to another method, after the zeolite has become saturated with $H_2S$, $CO_2$, $H_2O$, and any other impurities that may be present, a dry $N_2/O_2$ gas or air stream is heated to approximately 200° C., and then the gas is introduced into the zeolite bed. It is believed that one possible advantage of the second procedure over the first procedure is that the zeolite may be more uniformly heated, and consequently the desorption time is reduced and the zeolite may be regenerated more quickly.

Most, if not all, chemical reactions are influenced by the amount of heat generated by the reaction or that is present in the products or in the reactants. One purpose of the present invention is to increase the rate and efficiency at which heat is transferred from one area to another area.

According to one embodiment, the present invention provides heat-exchanger devices and an apparatus (e.g., a biogas conditioner) for heat management that uses the heat-exchanger device. Difficulties with heat management of zeolite are one of the main factors that must be overcome to improve the economic viability of purification of biogas using zeolite. Thus, one application of the present invention is heat management of zeolite, which is a molecular sieve that can be used to purify biogas produced by anaerobic digestion or from a sour gas well. In at least some embodiments, the present invention is not limited to the purification of biogas but has broad applications to any field or for any situation where heat management is an issue.

These and other benefits, advantages and features of the present invention will become more fully apparent from the following description and appended claims, or may be learned by the practice of the invention as set forth hereinafter.

BRIEF DESCRIPTION OF THE DRAWINGS

In order that the manner in which the above recited and other benefits, advantages and features of the invention are obtained, a more particular description of the invention briefly described above will be rendered by reference to specific embodiments thereof which are illustrated in the appended drawings. Understanding that these drawings depict only typical embodiments of the invention and are not therefore to be considered limiting of its scope, the invention will be described and explained with additional specificity and detail through the use of the accompanying drawings, in which:

FIG. 9 depicts an apparatus comprising a heat-exchanger and biogas conditioner with multiple units operated in parallel and/or series which is suitable for use at a municipal waste treatment facility;

DETAILED DESCRIPTION OF THE PREFERRED EMBODIMENTS

I. Introduction

The present invention can be broadly applied to any type of material that can exchange heat with another object. Some non-limiting examples include: zeolites, fluids, molecules, nanoparticles, mixtures, metals, and surfaces, such as the surface of a tube.

II. Exemplary Heat-Exchanger and Biogas Conditioner Devices

Figure 1:
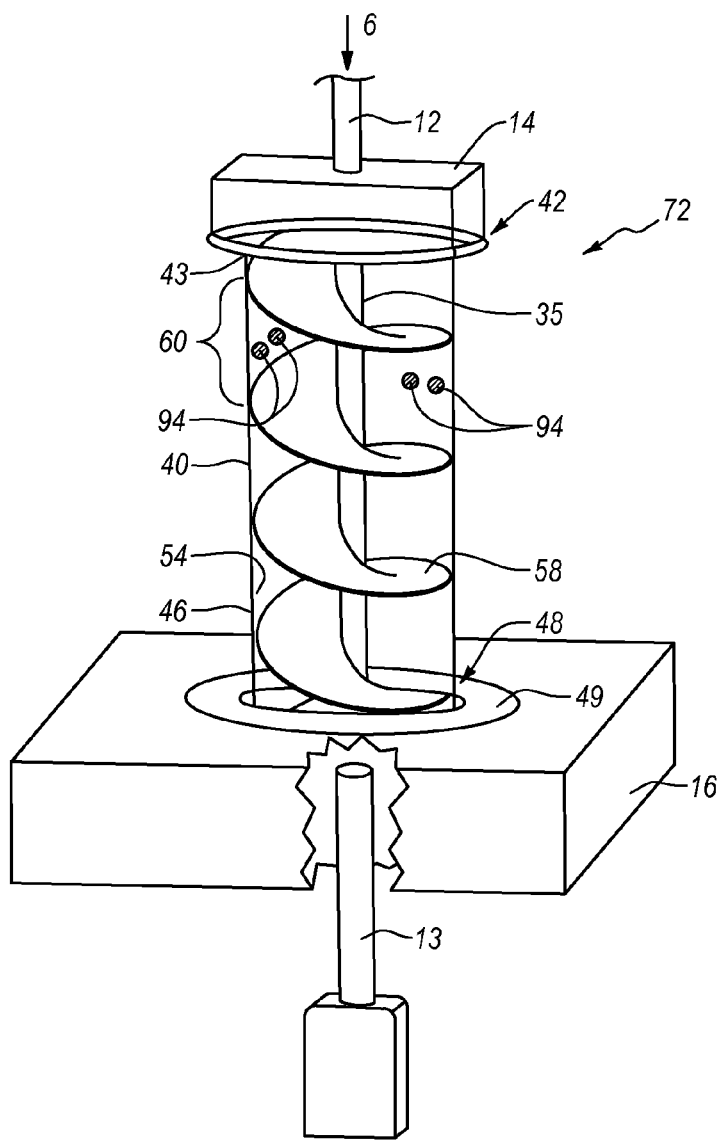
FIG. 1 is a perspective view of an exemplary heat-exchanger and biogas conditioner including a spiral fin configuration.
Figure 2:
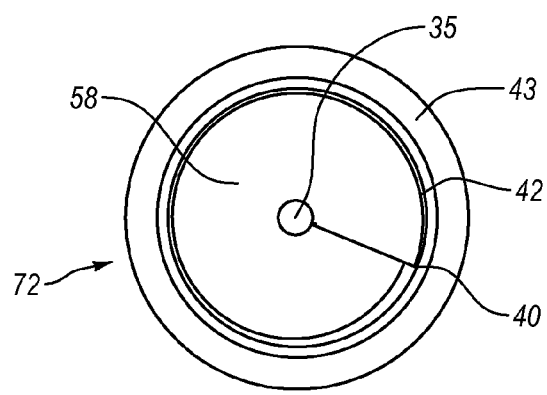
FIG. 2 is a top view of the heat-exchanger and biogas conditioner of FIG. 1.

FIGS. 1-2 depict one embodiment of an exemplary heat-exchanger 72, which can operate as a biogas conditioner as will be described below. Heat exchanger 72 comprises a heat exchange fin member 58 (e.g., in the shape of a spiral), an outer housing 40 (e.g., tube shaped), an upper flange 43, a lower flange 49, an upper manifold 14, and a lower manifold 16. An inlet 12 introduces impure biogas 6 into upper manifold 14, while an outlet 13 is disposed so as to collect conditioned biogas exiting through lower manifold 16. Of course, in an alternative embodiment the flow direction may be reversed. In some embodiments, the flanges 43, 49 are plates or collars which provide a seal between the respective manifolds and the respective ends of outer housing 40. The spiral fin 58, the outer housing 40, the upper flange 43, and the lower flange 49, as well as any other structures which contact the contents (e.g., zeolite) within the interior of heat exchanger 72 are preferably configured from metal, such as aluminum or an aluminum alloy having a relatively high thermal conductivity (e.g., at least about 50 W/m–K). Although the outer housing 40 preferably comprises a cylindrical tube, it may alternatively be rectangular or of any other shape.

Spiral shaped fin 58 is one example of a heat exchange member. In some embodiments, the surface of the spiral fin 58 is substantially flat. In other embodiments, the surface of the spiral fin 58 may be curved (e.g., similar to the curvature of an airplane wing). Other embodiments of spiral fin 58 may include other configurations that are similar to rotors, auger blades, motor blades, and other objects. In some of the most preferred embodiments, the spiral fin 58 is shaped like a fixed-auger blade (i.e., that is non-rotating) and comprises at least one level 60 (e.g., the example shown in FIG. 1 includes four levels). In one embodiment, the spiral fin 58 may be welded or otherwise attached to portions of the interior surface 54 of the outer housing 40. Each level 60 of spiral fin 58 may be defined by the section of the spiral fin 58 which begins at the point of contact between the outer housing 40 and the spiral fin 58 and ends at the next point of contact between the spiral fin 58 and the same side of outer housing 40 which is 360 degrees from the first point of contact (e.g., directly below the first point of contact). A turn may be defined as a point on the spiral fin 58 that separates two adjacent levels 60. A spiral fin 58 with four levels has four turns and can be described in turns/ft, that is, the number of fins divided by the vertical length of the spiral fin 58 as measured in feet. Preferably the spiral fin 58 is substantially surrounded by the outer housing 40, and the spiral fin 58 may spiral from the top end 42 of the outer housing 40 to the bottom end 48 of the outer housing 40.

The spiral fin 58 may be configured so that rounded objects (e.g., zeolite pellets) loaded at the top end 42 of the outer housing 40 will roll down along the path of the spiral fin 58 to the bottom end 48. Zeolite 94 (see FIG. 1), or some other material that exchanges heat, can be loaded into the heat-exchanger 72, filling heat-exchanger 72 from bottom end 48 upwards. Such a configuration is particularly useful for replacing the zeolite or other substance. A capping mechanism such as a wire screen 3 (see FIG. 8) disposed at or generally near the bottom end 48 of the outer housing 40 may be provided to prevent the zeolite 94 or other substance from rolling down the spiral fin and out of the outer housing 40 onto the floor. In one embodiment, substantially the entire height of outer housing 40 may be filled with a packed bed of zeolite 94 or other material.

In one embodiment, at least a portion of the spiral fin 58 contacts the interior surface 54 of the outer housing 40. The spiral fin 58 may comprise a material such as a metal that is selectively configured to maximize heat transfer to or from the zeolite 94 or other substance within the heat-exchanger 72 to the exterior surface 46 of the outer housing 40. Furthermore, the outer housing 40, the spiral fin 58, and any other structures configured to contact the zeolite 94 (e.g., an inner elongate-member 35) may be constructed from a material having a relatively high thermal conductivity. Preferred materials include metals, particularly aluminum and alloys thereof. Preferably, the selected material has a thermal conductivity of at least about 50 W/m-K, more preferably at least about 100 W/m-K, and most preferably at least about 150 W/m-K. 6061 Aluminum alloy is an example of one suitable aluminum alloy. It exhibits good strength, machinability, weldability, corrosion resistance (e.g., resistance to $H_2S$ corrosion) and a thermal conductivity of about 180 W/m-K.

A wire screen 3 (FIG. 8) may be provided so as to cap the bottom end 48 of the outer tube 40 so as to prevent zeolite 94 or other materials loaded within the outer housing 40 from falling out of the bottom end 48. Wire screen 3 may be removable, which is advantageous when replacing the zeolite 94. When the zeolite 94 is regenerated, the wire screen 3 does not necessarily have to be removed. Wire screen 3 at the bottom end of the outer housing 40 may comprise a relatively flat piece of wire screening that is generally the same shape and size as the bottom rim 41 (FIG. 8) at the bottom end 48 of outer housing 40. In one embodiment, wire screen 3 may be symmetrical and include a cut down the middle so as to form two pieces. A centrally disposed hole 36 (FIG. 8) for inner elongate-members 35, such as a rod, pipe, or tube, may be configured through the center of wire screen 3. Providing a cut down the middle of wire screen 3 enables the user to pull on the edges of the wire screen 3 to separate and remove the wire screen 3 from the bottom end 48 of outer housing 40. If the heat-exchanger has an outer housing 40 but does not include any inner elongate-member(s) 35, then the wire screen 3 may simply be configured to substantially match the size and shape of the rim 41 of the bottom end 48 of the outer housing 40 without the presence of any central hole 36. Wire screen 3 allows passage of conditioned biogas through the bottom end 48 of outer housing 40 and into lower manifold 16. Alternative structures (e.g., a perforated plate) that will be apparent to one of skill in the art may alternatively be used.

In one embodiment, the spiral fin 58 physically contacts the outer housing 40. For example, spiral fin 58 may be welded to the interior surface 54 of the outer housing 40. Such a configuration providing contact between spiral fin 58 and outer housing 54 is advantageous because heat can then be transferred more efficiently to the outer housing 40 from a bed of zeolite 94 or other substance that is in contact with the surface of the spiral fin 58. More efficient heat transfer to the outer housing 40 will allow waste heat to be dissipated relatively quickly. Of course, such physical contact provides for efficient heat transfer in the opposite direction as well (e.g., during regeneration of the zeolite bed 94) where the outer housing 40 may be heated.

In one embodiment, the temperature of the zeolite bed or other substance that contacts the spiral fin 58 is kept at or below approximately 40° C. during biogas conditioning. Because the reaction by which contaminants within a biogas stream are absorbed by the zeolite bed 94 is exothermic, it is advantageous to draw away excess heat so as to maintain the temperature of the heat-exchanger 72 (particularly zeolite bed 94) at a relatively low temperature. Maintaining the temperature below about 40° C. prevents the reaction rate from slowing substantially and/or ceasing to proceed in the desired direction. More preferably, the temperature of zeolite bed 94 is maintained at or below about 30° C. for optimal results.

The upper and lower flanges 43 and 49 respectively, may be torus-shaped, like a doughnut, and may form collars that surround the upper end 42 and lower end 48 of the outer housing 40. In one embodiment of the invention, the upper and lower flanges are circular and relatively thin. Preferably, upper flange 43 is configured so as to include a circular annular space at the center of upper flange 43. The top rim 42 of the outer housing 40 may be bolted or otherwise attached to the upper flange 43, which may be attached to upper manifold 14. The lower flange 49 may be similarly configured. Lower flange 49 may be bolted or otherwise attached to a lower manifold 16, which may be, among other things, a tabletop-like surface, a large container that is configured to contain gaseous substances, or a hollow container that is shaped like an inverted sandbox (e.g., so as to include downwardly oriented sidewall baffles).

In this type of configuration and depending on the dimensions of lower manifold 16, a plurality of heat-exchangers 72 may be removably connected to the lower manifold 16. Lower manifold 16 may be configured to include a corresponding number of annular spaces or recesses that are substantially the same size and shape as the bottom end 48 of the outer housing 40 so that the bottom end 48 of the inner space of each heat-exchanger 72 communicates with the inner space of lower manifold 16. A similar configuration could be provided between upper manifold 12 and the upper rim 42 of heat-exchanger 72.

In this type of configuration, gases could then relatively easily flow from any pipes or other inlets 12 that feed into the upper manifold 14, down through the outer housing 40, through a zeolite bed 94 or bed of other substance disposed within outer housing 40 and adjacent spiral fin 58. Furthermore, one or more fans may blow cool air across the outer surface 46 of outer housing 40 so as to maintain the temperature of the zeolite, or other contents at or below a desired temperature (e.g., approximately 40° C., more preferably at or below about 30° C.). Efficient heat management of the zeolite or other contents is best provided where the distance from any given location is within about 3 inches or less of the spiral fin 58 and/or housing 40. Even more preferably, the distance from any given location of zeolite bed 94 is within about 1.5 inches of spiral fin 58 and/or housing 40. For example, the distance between adjacent levels of spiral fin 58 may be no more than about 3 inches, which provides a distance from any given location within zeolite bed 94 to the spiral fin of about 1.5 inches or less. The close proximity of any given location within the zeolite bed relative to the high thermal conductivity surfaces of spiral fin 58 and/or outer housing 40 advantageously provides for efficient heat transfer of excess heat generated during adsorption by the zeolite out of the system or for heating the zeolite during regeneration.

As impure biogas 6 passes through the zeolite bed 94, the zeolite 94 captures all or substantially all of the impurities, i.e., $H_2S$, $CO_2$, $H_2O$, and any other impurities that may be present. This results in a substantially pure biogas stream, which exits the spiral fin heat-exchanger 72 and journeys through a pure biogas outlet tube 13 where it may subsequently be collected for storage. For example, preferably, at least about 90% of $H_2S$, $CO_2$, $H_2O$, and any other impurities that may be present are thus captured. More preferably at least about 95% of $H_2S$, $CO_2$, $H_2O$, and any other impurities that may be present are thus captured. Most preferably at least about 99% of $H_2S$, $CO_2$, $H_2O$, and any other impurities that may be present are thus captured. For example, $H_2S$ may be present within the conditioned output stream at about 5 ppm or less, more preferably about 1 ppm or less. $H_2O$ may be present within the conditioned output stream at about 6500 ppmv (parts per million by volume) or less, more preferably about 1500 ppmv or less.

In one embodiment of the invention, the spiral fin 58 comprises aluminum and the outer edges of each level of the spiral fin 58 are in contact with the inner surface 54 of the outer housing 40. By contacting the outer edges of the spiral fin 58 with the inner surface 54 of the outer housing 40, heat is transferred more effectively from the zeolite 94 (or other substance) to the spiral fin 58, and then to the outer housing 40. The exchange of heat could also proceed in the reverse direction, that is from the outer housing 40 to the spiral fin 58 and to the bed of zeolite 94 or other material (e.g., during regeneration of the packed zeolite bed 94).

For example, in one embodiment, a three-turn spiral fin 58 includes three layers or turns. Preferably, the vertical distance between two adjacent layers or turns is optimized so as to be about 6 inches or less. Such a configuration provides that at any given location, the zeolite or other material contained within the heat exchanger 72 is no more than about 3 inches from the spiral fin 58. The inventors have found that if the zeolite 94 (or other substance) is about 3 inches or less away from the spiral fin, then the rate at which heat is transferred from the zeolite (or other substance) to the spiral fin is more efficient. As described above, more preferably the vertical distance between two adjacent layers of fin 58 is about 3 inches or less so that at any given location, the zeolite 94 or other such material is no more than about 1.5 inches from spiral fin 58.

For larger outer housings 40, the inventors have further found that even where adjacent layers of the spiral fin are no more than about 6 inches apart, it may be helpful to provide at least one inner elongate-member 35 (e.g., a hollow tube or solid rod), for example, configured to run along the longitudinal axis of the outer housing 40. Although such a configuration may be preferred, alternative configurations may provide one or more inner elongate-members that run vertical, horizontal, and/or skewed that do not bisect the central diameter of the upper rim 42 or lower rim 48 of the outer housing 40. According to one embodiment, the ratio between the thickness of the spiral fin and the radius of a layer of the spiral fin may be about 1:10. Such a relatively thin thickness to radius (or length) ratio aids in providing good thermal conductivity characteristics to the structure.

Heat may be conducted into and/or dissipated from spiral fin 58 according to any of various techniques. In one embodiment, one or more fans may blow cool or hot air against the exterior of outer housing 40 and/or into the annular space within the packed interior of outer housing 40 so as to increase heat transfer by convection. In another embodiment, the heat exchanger 72 may be disposed in a tank of fluid (e.g., water, antifreeze coolant, or other substance) and the temperature of the water or other fluid could be elevated, reduced, or stabilized, depending on whether it is desirable for the temperature of the zeolite 94 or other substance to be lowered or raised. Such a configuration increases heat transfer as a result of convection and/or conduction into or from the adjacent fluid.

During use, impure biogas 6 is channeled, pumped, or pushed down (e.g., under pressure) so as to be introduced into the annular space of the outer housing 40. The spiral fin 58 is generally located inside the annular space of the outer housing 40 and preferably runs from the top end 42 to the bottom end 48 of the outer housing 40. As mentioned above, the outer housing 40 may be cooled from the outside using fans or other equipment (or by controlling the temperature of a body of water or other fluid wherein the outer housing 40 is submerged in that fluid). The size of the outer housing 40 may be configured so that the zeolite bed 94 or other substance is cooled or heated sufficiently. In some embodiments it may be advantageous to provide an inner elongate member 35 (e.g., a solid rod, a hollow tube, or a combination of solid rod(s) and hollow tubes) that runs along the longitudinal axis of the outer housing 40. Such a structure provides an additional surface exhibiting a relatively high thermal conductivity so as to more efficiently transfer heat into or out of the zeolite bed 94.

One relatively simple configuration may include a single spiral fin heat-exchanger; however, other configurations could be implemented, such a two-unit apparatus, a three-unit apparatus, etc. The spiral fin heat exchangers could be aligned linearly, in a rectangular shape, in an X-shape, in clusters, in a generally circular shape, or in any other configuration.

In one embodiment, the exterior surface 46 of the outer housing 40 of the heat-exchanger may be wrapped or coiled in heating tape, cooling tape, a heating element (e.g., a heating coil), or cooling element (e.g., a cooling coil), such that the temperature of heat-exchanger 72 may be manipulated by adding or removing heat from the system through the cooling tape, cooling coil, heating tape, or heating coil. Of course, heat may also be removed by any suitable heat sink (e.g., submersion in a fluid bath). In some embodiments, the heating tape comprises a ceramic cloth that is weaved with metals such as nickel chromium. When current is passed through the heating tape, electrical resistance results in release of heat. Alternatively, in other embodiments, the outer housing 40 could be wrapped with thermal paper. In some embodiments, wires or other structures that are configured to be embedded internally in the tapes or coils can be heated or cooled.

In one embodiment, at least one opening, hole, or annular space 90 (FIG. 3) is provided along the spiral fin 58. In the absence of holes or annular spaces 90 in the spiral fin 58, when impure biogas 6 enters through the top rim 42 of a heat-exchanger 72, the impure biogas 6 will follow the path of the spiral fin 58 and contact any zeolite 94 or other packing material that is in contact with the spiral fin 58. Thus, the path that the impure biogas 6 must travel is maximized because the impure biogas 6 is bounded by the spiral fin 58 and outer housing 40. In some embodiments, the spiral fin 58 comprises metal wire (e.g., a screen like-material) or has a plurality of holes/annular spaces in the actual spiral fin 58 itself. Providing such a discontinuous boundary surface allows the impure biogas 6 to travel multiple routes through the zeolite bed 94 (or bed of other material). For example, instead of following a strictly helical or spiral path, some of the impure biogas 6 is able to travel in the vertical direction through the holes and then continue in a helical path along the spiral fin towards the bottom of the outer housing 40.

In some embodiments, inner elongate-members (e.g., inner rod 35), such as pipes, solid rods, and/or hollow tubes, are provided within outer housing 40. Such inner elongated-member(s) and the outer housing 40 may have longitudinal axes which are coaxially aligned relative to one another. In other embodiments, inner elongate-members connect between a location on the inner surface 54 of the outer housing 40 with another location on the inner surface 54 of the outer housing 40. Such inner elongate-members may be formed of a metal exhibiting relatively high thermal conductivity (e.g., comprising aluminum). One purpose of such inner elongate-members is to increase the available area over which heat exchange can occur between zeolite 94 or other contained substances and the heat-exchanger 72. For example, zeolite 94 is a ceramic material that is largely insulative (i.e., exhibits a relatively low thermal conductivity as compared to the metal materials of spiral fin 58, outer housing 40, and any elongate-members).

In some embodiments, solid rods run vertically through the annular space of the outer housing 40. Such solid rods may be constructed from a metal exhibiting a relatively high thermal conductivity such as aluminum or alloys thereof. Heating or cooling of such solid rods allows heat to be transferred to or from the zeolite bed 94 within heat-exchanger 72 to the surrounding environment.

In other embodiments, at least some of the solid rods may be replaced with hollow tubes, and various substances may be pumped through or allowed to pass through the hollow tube(s). Some nonlimiting examples of heating or cooling fluids that may be passed through such a hollow tube include, but are not limited to, hot air, hot water or other liquid, cooled water, ice, cold air, cold water or other liquid (e.g., anti-freeze and/or ethylene glycol). Generally, substances at ambient temperature, substances below ambient temperature, substances above ambient temperature, ambient fluid (e.g., liquid or gas), etc. may be used. Heating or cooling elements (e.g., tape or coil) may also be provided so as to heat or cool such a hollow tube.

Figure 3:
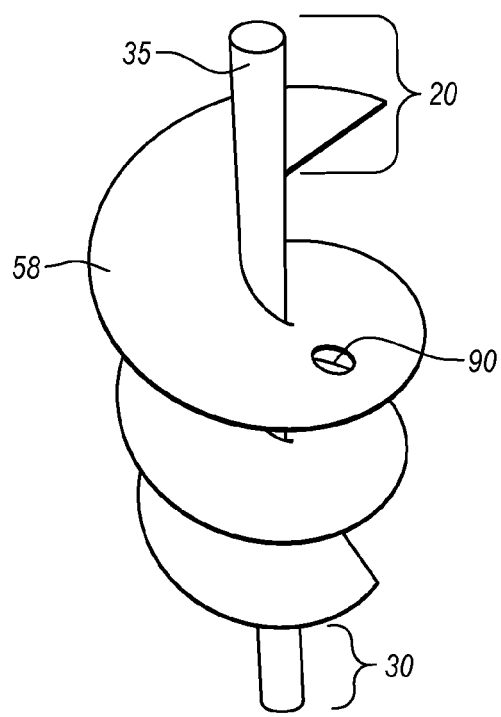
FIG. 3 is a perspective view of an exemplary spiral fin of the heat-exchanger and biogas conditioner of FIG. 1.
Figure 4:
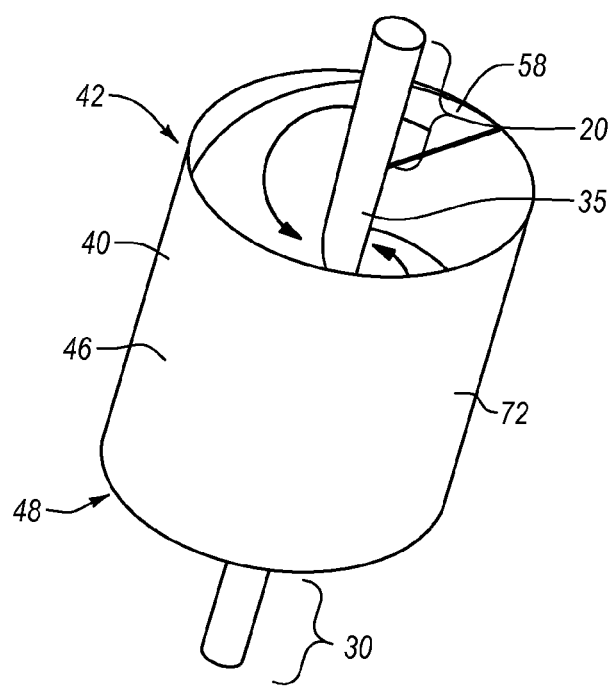
FIG. 4 is a perspective view of an exemplary spiral fin and outer housing similar to that of FIG. 3, but also including an inner elongate-member around which the spiral fin is disposed.

In some embodiments, an inner hollow tube is employed, the inner hollow tube contacts the spiral fin 58, and as the inner hollow tube changes temperature, the spiral fin 58 and objects that are in contact or near contact (e.g., zeolite 94) with the spiral fin 58 will also change temperature. If a hollow tube is used to convey fluids or even solids, then hollow tubes from multiple heat-exchangers 72 could combine (e.g., communicate) into a single hollow tube and the single hollow tube can then go through a single hole in the upper manifold 14 or lower manifold 16. Alternatively, in other embodiments, a plurality of elongate-members 35, such as hollow tubes, rods, or pipes, can exit the bottom end of the outer housings 40 and can then exit through an opening in the lower manifold 16, and then finally join together into a single tube. As shown in FIGS. 3-4, an upper-extending portion 20 of an elongate-member 35 may extend beyond the top of fin 58 and/or outer housing 40. Likewise, a lower-extending portion 30 of an elongate-member 35 may extend beyond the bottom of fin 58 and/or outer housing 40.

In some embodiments of the invention, it is believed that voids, pockets or air, and pockets of gas in the heat-exchanger 72 should be minimized or avoided because uniform distribution of the zeolite 94 or other substance generally provides better absorption of undesirable components within the biogas 6, while also providing for more efficient transfer of heat to or from the zeolite bed 94. One method for minimizing or avoiding formation of such pockets is to pack the zeolite into the outer housing 40 so that the number of voids in the zeolite (or other substance) bed is minimized. Settling and packing of the zeolite 94 may be improved by shifting or shaking the apparatus after or during loading.

The following references contain information about adsorption, zeolites, and other useful information and are incorporated herein by specific reference: 1) Adsorption by powders & porous solids: principles, methodology and applications. Françoise Rouquerol, Jean Rouquerol and Kenneth Sing. Publisher: San Diego, Calif.: Academic Press, 1999. ISBN: 0125989202. 2) Gas separation by adsorption processes. Ralph T. Yang. Publisher: Boston: Butterworths, 1987. ISBN: 0409900044.

Zeolites refer to a class of aluminosilicate microporous molecular sieves. The term molecular sieve refers to the ability of such materials to selectively sort molecules based primarily on a size exclusion process. This is due to a very regular pore structure of molecular dimensions within the zeolite. Generally, the maximum size of the molecular or ionic species that can enter the pores of a zeolite is controlled by the dimensions of the channels. These are conventionally defined by the ring size of the aperture, where, for example, the term "8-ring" refers to a closed loop that is built from 8 tetrahedrally coordinated silicon (or aluminum) atoms and 8 oxygen atoms. These rings are not always perfectly symmetrical due to a variety of effects, including strain induced by the bonding between units that are needed to produce the overall structure, or coordination of some of the oxygen atoms of the rings to cations within the structure. Therefore, the pores in many zeolites are not cylindrical.

Any suitable zeolite or other molecular sieve material may be used within the apparatus of the present invention. As such, the term "zeolite" as used herein is to be broadly construed so as to refer to any sorbent that binds $H_2S$, $CO_2$, $H_2O$ and/or other contaminants within a biogas or other sour gas stream. The binding may be non-covalent, and preferably exhibit a relatively large enthalpy change for binding. Generally, the larger the enthalpy change, the better the sorption and selectivity, which also requires a smaller temperature change for regeneration.

Figure 5:
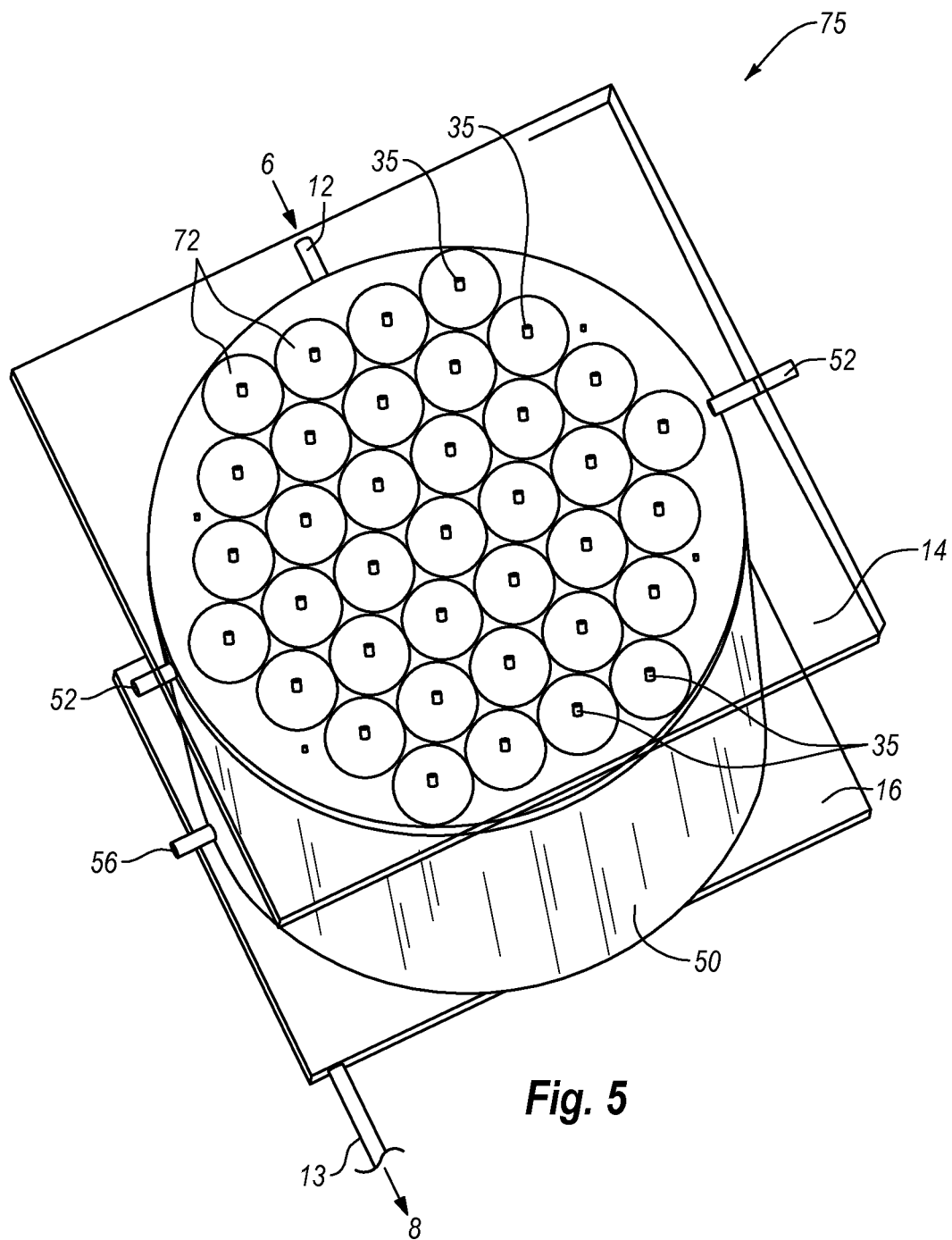
FIG. 5 is a top perspective view of an apparatus that comprises a plurality of spiral fin heat-exchanger and biogas conditioner devices similar to that shown in FIG. 1.
Figure 6:
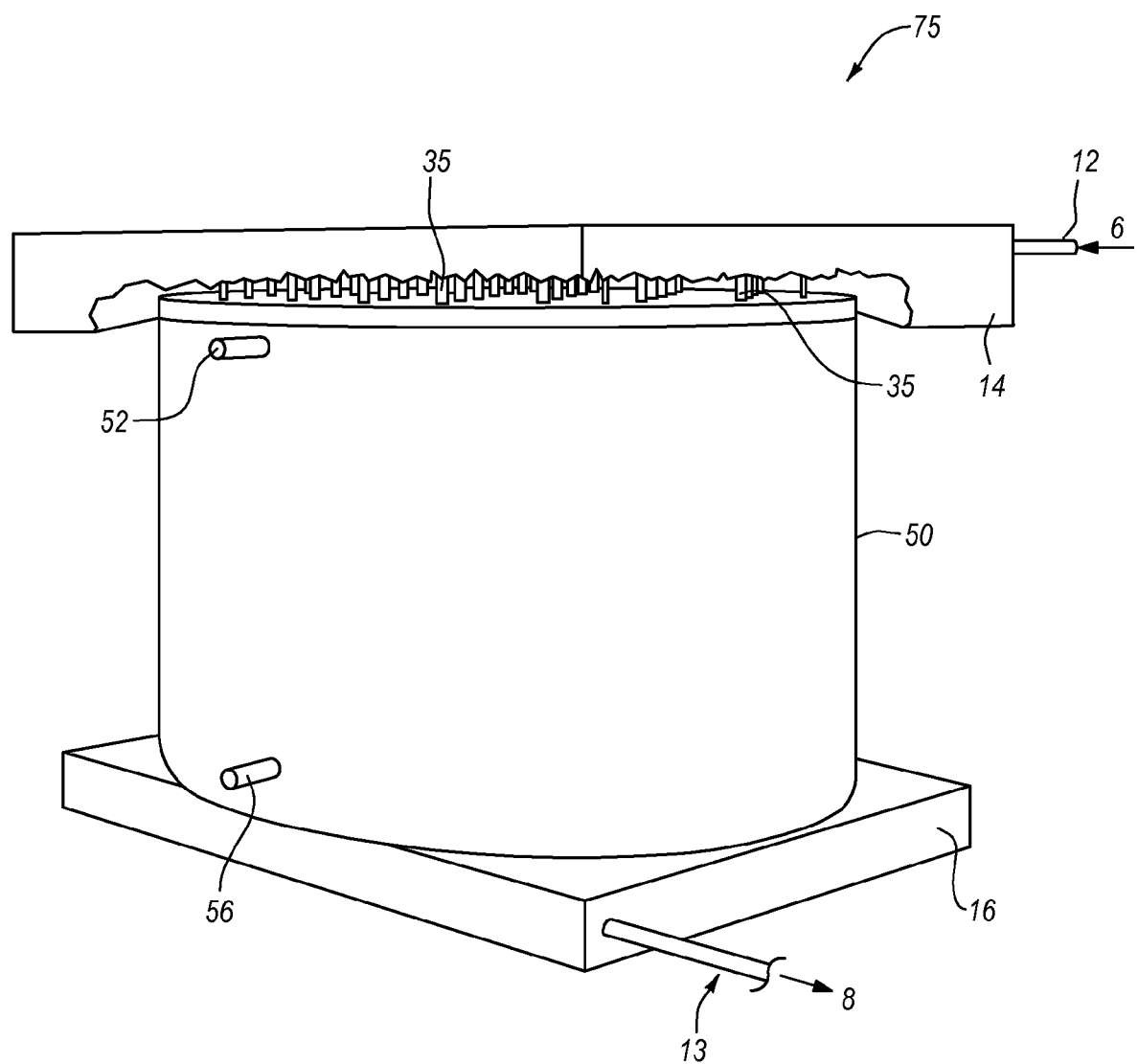
FIG. 6 is a different perspective view of the apparatus in FIG. 5.

According to one particularly preferred method of use, the heat-exchanger 72 comprises a biogas conditioner 72 configured to purify impure biogas 6. As shown in FIGS. 5-6, in a multi-unit system including more than one unit, an outer shell 50 may be provided within which the plurality of heat-exchanger units 72 are disposed. FIG. 5 shows an exemplary embodiment including 37 units surrounded by a shell 50. The shell 50 surrounds the array of heat-exchangers 72. In one embodiment, the shell 50 may be cylinder shaped without a top or bottom face. At least one inlet 52 may be provided to convey cold air, hot air (e.g., diesel engine exhaust), ambient air, or other substances at a desired temperature into the interior space bounded by shell 50. One or more outlets 56 may similarly be provided to remove such substances from the interior of shell 50.

In some embodiments, the area bounded by the shell 50, upper manifold 14, and lower manifold 16 acts as a single container so that substances that are introduced through the inlet(s) 52 will also reach the zeolite 94 or other contained substance and aid in heat exchange to or from the zeolite 94. An upper manifold 14, which may be similar to a large, shallow inverted box without a lid, may be positioned selectively on the top of the shell 50. Lower manifold 16 may be similarly configured. The lower manifold 16 may comprise four walls and a bottom panel. The walls and panel include interior and exterior surfaces, and the interior surface of the walls and bottom panel define an interior space which is bounded by the four walls and the bottom panel. When the upper manifold 14 is connected to the top of the shell 50, the upper manifold 14 may act as a temporary storage container for impure biogas 6 or other substances.

Figure 7:
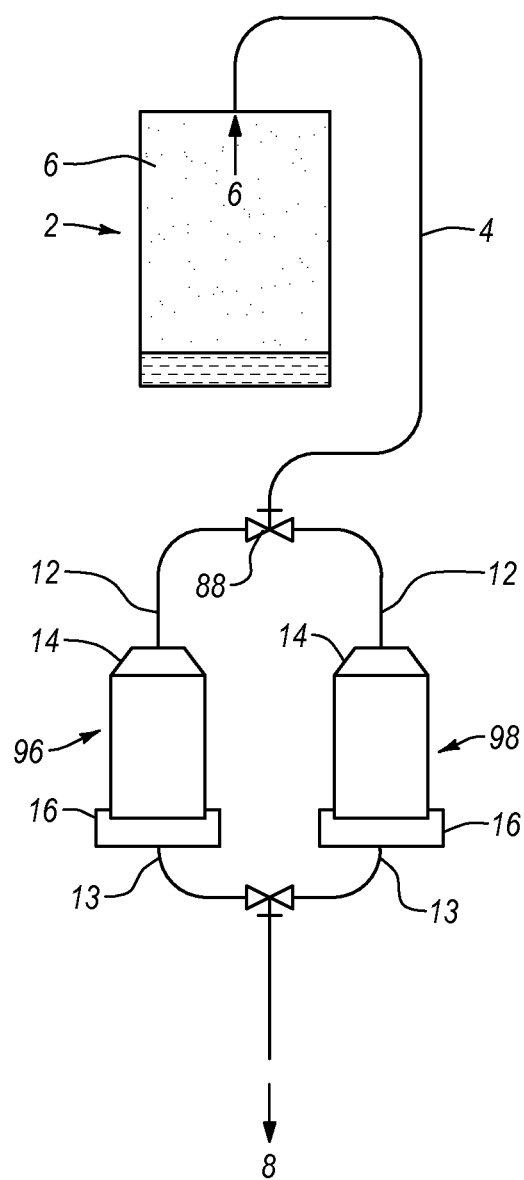
FIG. 7 is a schematic diagram depicting an anaerobic digester and two biogas conditioners.

As seen in FIG. 7, in one embodiment, the inlet 12 of upper manifold 14 may be connected to an anaerobic digester 2 by a tube 4 or other mechanism. In some embodiments as the digester 2 produces impure biogas 6, the biogas 6 moves through the digester-manifold connecting mechanism 4, through inlet 12, and into the annular space defined by upper manifold 14, which may also be constructed of aluminum or an aluminum alloy. A tap, valve or other controlling mechanism may be used to allow biogas 6 to flow through the digester-manifold connecting mechanism 4 and may also be used to prevent the flow of biogas 6 when desired. After a period of time, the manifold generally builds up at least a few PSI of pressure as a result of biogas pressure into the upper manifold 14. The build-up of pressure forces impure biogas 6 and any air in the manifold to move down the outer housings 40 of the heat-exchangers 72. A bed of zeolite 94 or other material packed within and in contact with the spiral fin, removes most or nearly all impurities within biogas 6 as the biogas passes through the zeolite bed 94 (or other material). As the cleaned biogas 8 exits the outer housing 40 at the bottom end of the outer housing 40, the conditioned biogas 8 is collected from the various units 72, exiting through outlet 13. The conditioned biogas 8 is substantially more pure than the impure biogas 6 that entered the upper manifold (i.e., the biogas has less carbon dioxide, $H_2S$, water, and/or other impurities than the impure biogas 6 prior to conditioning). The result is that conditioned (e.g., substantially pure) biogas 8 is less likely to damage a power generation turbine or other equipment during combustion. For example, $H_2S$ may be present within conditioned biogas stream 8 at about 5 ppm or less, more preferably about 1 ppm or less. $H_2O$ may be present at about 6500 ppmv or less, more preferably about 1500 ppmv or less.

In some embodiments, one or more inner elongate members (e.g., hollow inner tubes 35) are used to introduce cold or hot fluid (e.g., air and/or water) into the spiral fin heat-exchangers 72. Hollow inner tubes 35 may each be associated with a respective spiral fin heat-exchanger 72, which tubes could then be joined together into a single pipe. In some embodiments, the outer housing 40 of the spiral fin heat-exchangers 72 are connected to a flange, and the flange is connected to the respective manifold. In some embodiments, the hollow inner tubes 35 join together into a single pipe inside the interior space of the manifold, and then that single pipe exits the manifold at a single point. In other embodiments, the hollow inner tubes 35 each exit the manifold through an opening and then join together into a single pipe which is located outside the manifold.

Cold, hot, or ambient fluid (e.g., air and/or water) may be pumped through the inner hollow tubes 35 to increase the rate of heat exchange into or out of the zeolite 94. For example, cool or ambient temperature water may be circulated through hollow inner tubes 35 of each heat-exchanger 72, and the water is heated as it passes through the hollow inner tubes 35 as heat is drawn away from the zeolite 94. The heated water may then be conveyed to a radiator or other heat exchange mechanism where the heated water is cooled for reuse. Where a continuous source of water is available, the water may not be recycled.

In one embodiment, inner hollow tube 35 may be limited to about 0.5 inch to about 2.5 inches in outside diameter. The optimal flow rate of the biogas 6 through the zeolite bed 94 (or other contained substance) will be calculable to a person of ordinary skill in the art in light of the present disclosure. Such calculations may generally include such factors as the enthalpy change for the binding (i.e., adsorption) reaction, the binding constant, any temperature dependence of the binding constant, and the kinetics of binding the impurity to be removed.

In one embodiment, cooling or heating fluids or other substances may be flushed into the annular space of the outer shell 50 so as to aid in heating or cooling each heat exchanger 72 and its contents (e.g., through inlet 52 and outlet 56). In such embodiments it may be preferable to seal the annular space within each housing 40 of each unit 72 so as to prevent the cooling or heating fluid from comingling with the biogas 6 passing through the zeolite packed bed 94.

FIG. 7 shows a particularly preferred configuration including at least two biogas conditioners. A single pipe 4 may feed from anaerobic digester 2 through a valve 88 and into the first biogas conditioner 96. When the first biogas conditioner 96 needs to be regenerated because zeolite 94 can no longer efficiently adsorb impurities, valve 88 is activated so that impure biogas 6 is conveyed to second biogas conditioner 98. First biogas conditioner 96 can then undergo regeneration while the second biogas conditioner 98 is used to purify the impure biogas 6. The process may then be switched once the zeolite bed of first biogas conditioner 96 has been regenerated (that is, returned to a state where it can efficiently adsorb and trap impurities) and/or the zeolite 94 of second biogas conditioner 98 requires regeneration. Thus, two or more biogas conditioners may be configured in parallel so as to allow continuous operation, even while the zeolite of one of the conditioners is being regenerated.

Figure 8:
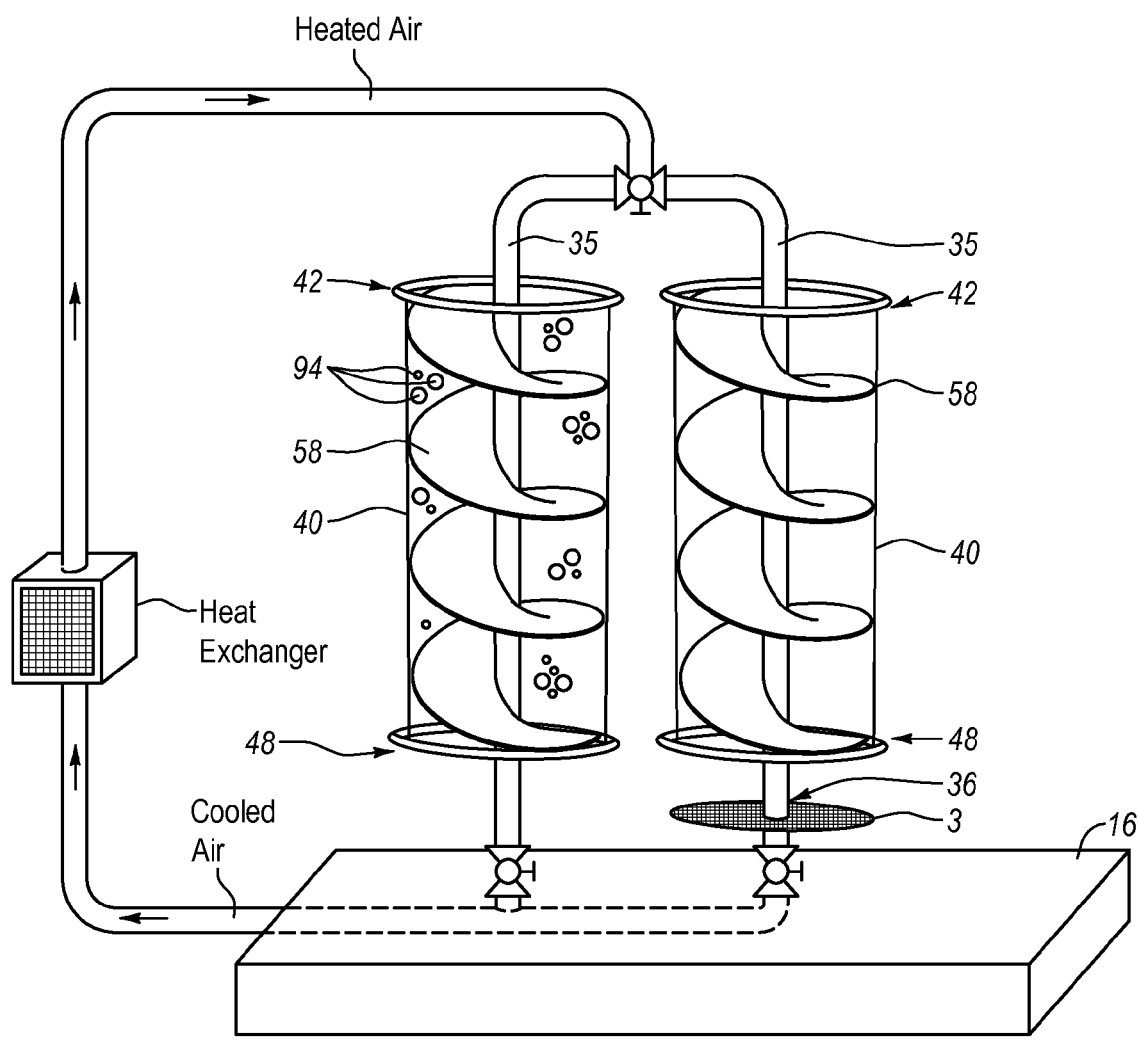
FIG. 8 is a close up perspective view of two biogas conditioners, one of which is being processed through a regeneration cycle.

For example, as shown in FIG. 8, heated air from a heat exchanger (or generated from the other operating biogas conditioner) may be used to heat zeolite bed 94, releasing bound impurities. For example, the unit on the left may be undergoing regeneration of the zeolite 94 while the unit on the right conditions a biogas stream. Released impurities may be collected and disposed of as desired (e.g., further processed into value added product, sequestered, vented, etc.).

In one embodiment, each biogas conditioner 96, 98 includes a heating coil or other heating element (e.g., heating tape), for example, disposed around and/or in contact with outer housing 40. When the heating element is heated, heat is transferred to the outer housing 40 of the respective biogas conditioner. According to Le Chatlier's principle, since the reaction by which impurities within the biogas 6 are adsorbed within zeolite is exothermic (i.e., heat is produced), it follows that by adding sufficient heat to the system (for example, by turning on the heating tape or heating coil) then the equilibrium of the reaction is shifted in the opposite direction so that any impurities from the biogas that are trapped inside the zeolite 94 may be released.

In the more preferred embodiments, the following equation is applicable:

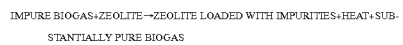

IMPURE BIOGAS+ZEOLITE→ZEOLITE LOADED WITH IMPURITIES+HEAT+SUBSTANTIALLY PURE BIOGAS

Thus, the loaded zeolite may be regenerated by adding heat (such as hot air, hot liquid, or application of heat through a heating coil or tape) into the outer housing 40 of the respective biogas conditioner 96, 98. In other embodiments, heat may be directed to both the interior of the outer housing 40 and to the exterior surface 46 of the outer housing 40. Heated air generated through the process (e.g., either from drawing heat away during adsorption or heated air used during regeneration of the zeolite) may be used to heat a building or other space. In some embodiments, the pipe containing the conditioned biogas 8 comprises one or more detectors to measure for impurities that may be present in the biogas. Such detectors may help control the quality of the conditioned biogas.

In other embodiments, the biogas may be circulated through the conditioners 96, 98 two or more times (i.e., recycled) to further decrease the amount of impurities in the biogas. Alternatively, two or more biogas conditioners may be configured in series so as to accomplish a similar result. In embodiments including a spiral fin heat exchange member, the fin 58 may be permeable (e.g., include holes of any desired size), and this may allow the impure biogas 6 to travel through the zeolite bed more rapidly since some of the biogas 6 could travel through holes 90 in the spiral fin. Such configurations may decrease residence time within the biogas conditioner, increasing throughput while decreasing adsorption and purity of the resulting conditioned biogas 8. In light of the present disclosure, it will be apparent to those of skill in the art that such parameters may be adjusted so as to achieve desired performance characteristics (e.g., desired purity, flowrate throughput, etc.).

In one example a plurality of spiral fin heat-exchangers 72 may be encased by a shell 50 and can be run for several hours in parallel before they need to be regenerated. For example, the embodiment shown in FIGS. 5 and 6 includes 37 individual heat exchanges 72 in parallel and may run for about 10 hours before requiring regeneration of the zeolite 94. The amount of run time before regeneration is needed may be calculated and/or discovered by routine testing by one of skill in the art in light of the present disclosure. Factors affecting run time between regeneration may include the volume or flow rate of biogas to be conditioned, the composition of the biogas, temperature of the system, the specifications of the selected zeolite or other contained material adsorbing the impurities, and other factors. All else being equal, an embodiment including only 3 spiral fin heat exchangers in parallel encased by a shell 50 will exhibit a significantly reduced run time between regeneration as compared to an example employing 37 biogas conditioners. Including more biogas conditioners in parallel increases the volume and/or flow rate of biogas that can be conditioned to a desired purity. Including additional biogas conditioners in series increases the level of purity within the conditioned biogas 8.

In some embodiments, the biogas conditioning apparatus may be adapted for home use by an individual user. In other embodiments, the biogas conditioning apparatus is scaled for use by municipal waste sewage treatments. Exemplary, non-exhaustive uses of the biogas conditioning apparatus include confined animal operations, municipal waste, municipal waste water, and sour natural gas wells (e.g., particularly off-electrical grid "orphan" wells). In one embodiment, the biogas conditioner that is described herein may be connected to a digester 2 (FIG. 7). For example, such a digester 2 may employ hydrogen peroxide or other processes to increase conversion of organic materials into methane and/or hydrogen. As shown in FIG. 9, multiple units 75 (e.g., such as those shown in FIGS. 5-6) may be operated in series and/or parallel so as to increase capacity for larger facilities and/or increase purity of the conditioned output stream.

In one embodiment, the system is designed to provide removal of $H_2S$ to below about 5 ppm. More typical performance may be below about 1 ppm. The system may provide removal of $H_2O$ to below about 6500 ppmv, with more typical performance to below about 1500 ppmv. An exemplary biogas stream to be treated may flow at about 750 ft³/day near atmospheric pressure at a temperature of at least about 35° C. (e.g., a digester may run at about 35° C. to about 45° C.) and that is saturated with water vapor on a continuous basis. The system may comprise controls, structure, and/or materials for collection of the product. For example, trapped $H_2S$ from the biogas conditioning system may be converted into elemental sulfur, which may then be discarded or sold as a value added product.

Figure 10A:
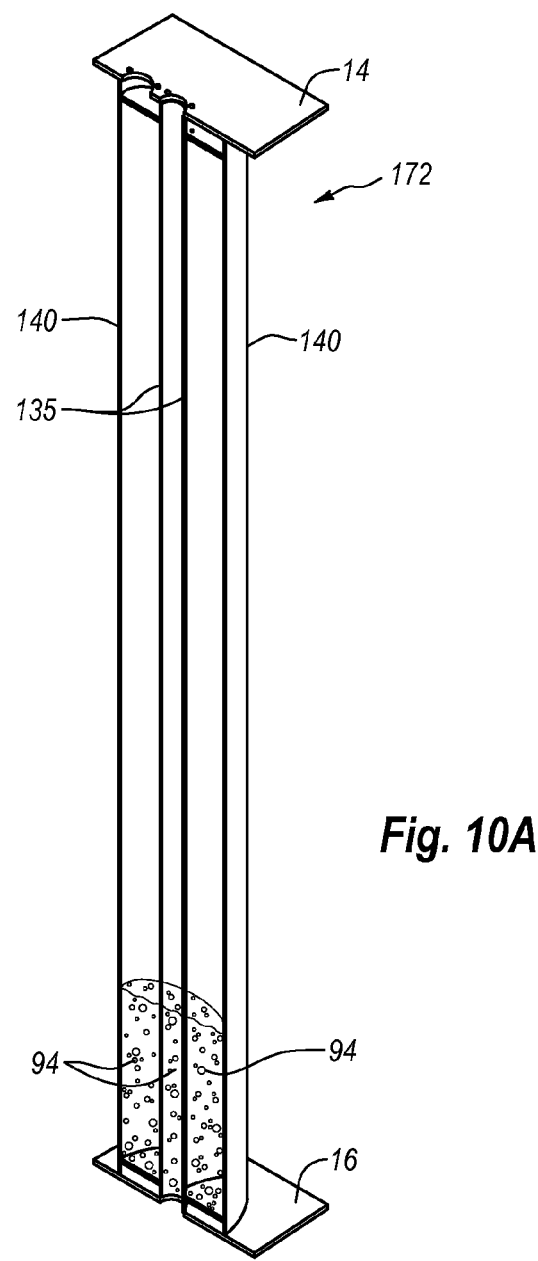
FIG. 10A is a perspective view of an alternative heat-exchanger configuration for use in a biogas conditioner according to the present invention.
Figure 10B:
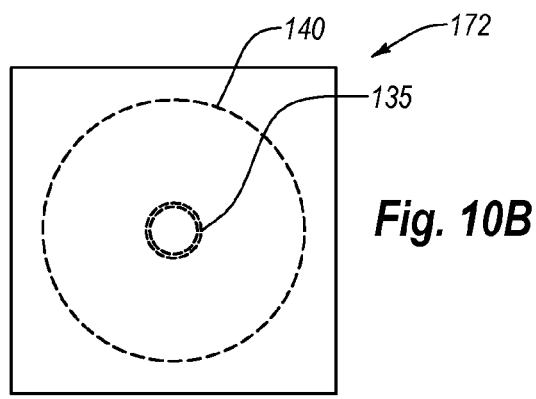
FIG. 10B is a top view of the heat-exchanger and biogas conditioner device of FIG. 10A.

FIGS. 10A-10B illustrate an alternative heat exchange member. Rather than including a spiral fin heat exchange member (which can be difficult and/or expensive to machine), the heat-exchanger 172 of FIGS. 10A-10B includes an outer housing 140 and an inner tube 135 disposed concentrically within outer housing 140. Both outer housing 140 and inner tube 135 are substantially cylindrical and hollow, so that a zeolite 94 may be loaded within inner tube 135, as well as within the annular space between outer housing 140 and inner tube 135. In FIG. 10A, heat-exchanger 172 is only shown partially filled for purposes of clarity, although it will be understood that preferably the zeolite bed 94 substantially fills the entire volume within inner tube 135 and outer housing 140. Both outer housing 140 and inner tube 135 are formed of a material having a relatively high thermal conductivity (e.g., at least about 50 W/m–K), for example aluminum and/or aluminum alloys.

Furthermore, the dimensions of outer housing 140 and inner tube 135 are specifically configured so that any given position within zeolite bed 94 is no more than about 3 inches, preferably no more than about 1.5 inches away from at least one of outer housing 140 or inner tube 135. Such a configuration allows for heat to be efficiently conducted away during adsorption processing of the biogas 6, as well as vice-versa during regeneration of the zeolite when it is necessary to efficiently heat the zeolite to drive off the adsorbed impurities. For example, in one embodiment, outer housing 140 has a diameter of about 8 inches, while inner tube 135 has a diameter of about 2 inches. Such a configuration provides no more than about a 3 inch separation between outer housing 140 and inner tube 135, so that even within the center of this separation, zeolite is only about 1.5 inches from either highly thermally conductive surface.

Figure 11A:
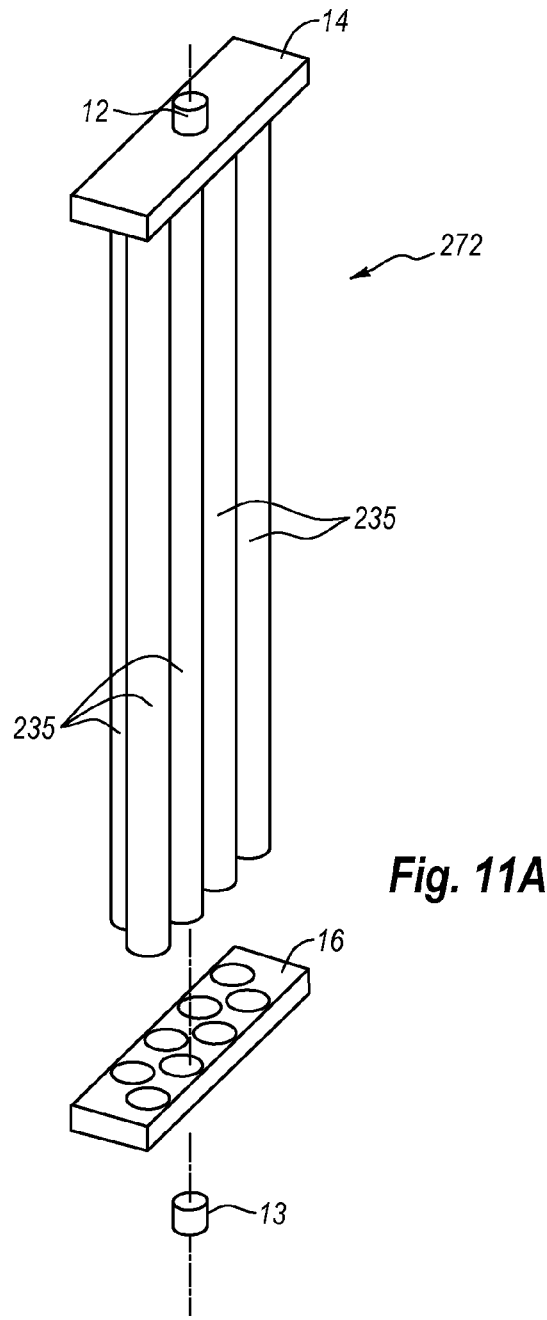
FIG. 11A is a perspective view of another alternative heat-exchanger configuration for use in a biogas conditioner according to the present invention.
Figure 11B:
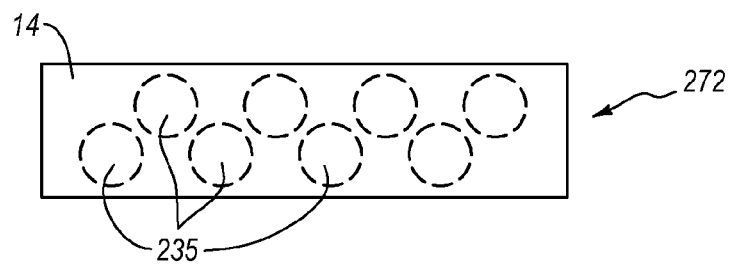
FIG. 11B is a top view of the heat-exchanger and biogas conditioner device of FIG. 11A.

FIGS. 11A-11B illustrate another alternative heat exchange member. The heat-exchanger 272 of FIGS. 11A-11B includes a plurality of tubes 235, each extending longitudinally between upper and lower manifolds 14, 16. Each tube 235 may be substantially cylindrical and hollow, so that a zeolite 94 may be loaded within each tube 235. Each tube 235 is formed of a material having a relatively high thermal conductivity (e.g., at least about 50 W/m–K), for example aluminum and/or aluminum alloys. An alternative embodiment may include an outer housing (not shown), for example rectangular or circular, depending on the arrangement of tubes 235, surrounding the plurality of tubes 235, and zeolite 94 may also be loaded within the space defined between outer housing and the plurality of tubes 235.

Furthermore, the dimensions of each tube 235 are specifically configured so that any given position within zeolite bed 94 contained within each tube is no more than about 3 inches, preferably no more than about 1.5 inches away from the surface of tube 235. Such a configuration allows for heat to be efficiently conducted away during adsorption processing of the biogas 6, as well as vice-versa during regeneration of the zeolite when it is necessary to efficiently heat the zeolite to drive off the adsorbed impurities. For example, in one embodiment, each tube 235 has a diameter of about 3 inches. Such a configuration provides no more than about a 3 inch separation between from tube 235 at any given point within zeolite bed 94, so that even within the center of this separation, zeolite is only about 1.5 inches from either highly thermally conductive surface.

Figure 12A:
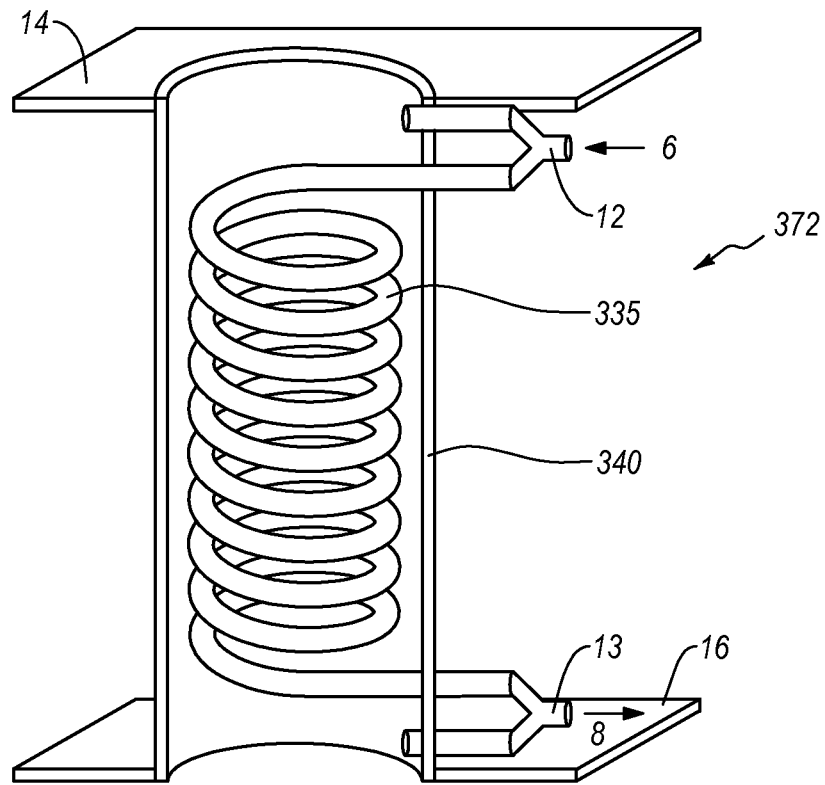
FIG. 12A is a perspective view of another alternative heat-exchanger configuration for use in a biogas conditioner according to the present invention.
Figure 12B:
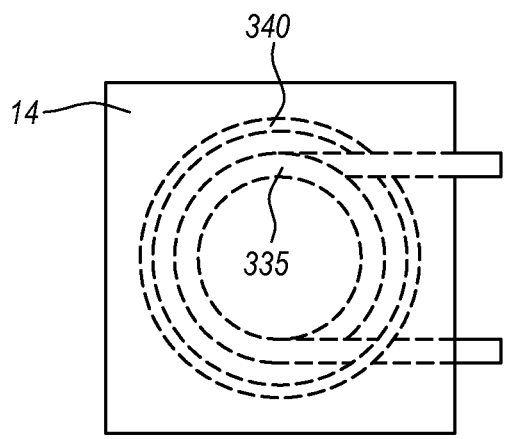
FIG. 12B is a top view of the heat-exchanger and biogas conditioner device of FIG. 12A.

FIGS. 12A-12B illustrate another alternative heat exchange member. The heat-exchanger 372 of FIGS. 12A-

12B includes an outer housing 340 and an inner tube 335 configured in a spiral configuration within the outer housing 340. Zeolite 94 may be loaded within spiral tube 335 as well as optionally within the space between outer housing 340 and spiral tube 335. Spiral tube 335 and optionally outer housing 340 are formed of a material having a relatively high thermal conductivity (e.g., at least about 50 W/m–K), for example aluminum and/or aluminum alloys. In an alternative embodiment, housing 340 may comprise an insulating material.

Furthermore, the dimensions of spiral tube 335 and optionally outer housing 340 are specifically configured so that any given position within zeolite bed 94 is no more than about 3 inches, preferably no more than about 1.5 inches away from at least one of the spiral tube 335 or outer housing 340. Such a configuration allows for heat to be efficiently conducted away during adsorption processing of the biogas 6, as well as vice-versa during regeneration of the zeolite when it is necessary to efficiently heat the zeolite to drive off the adsorbed impurities. For example, in one embodiment, spiral tube 335 has a diameter of about 3 inches. In embodiments where outer housing is not filled with zeolite 94, this provides about a 1.5 inch separation maximum between any given location of zeolite 94 and spiral tube 335. In embodiments in which the outer housing 340 is also loaded with zeolite 94, housing 340 is also formed of a thermally conductive material, and may be spaced so that no more than a 3 inch gap exists between spiral tube 335 and outer housing 340.

Each of the described configurations includes a heat exchange member disposed between the upper and lower flanges of the apparatus in which at least the heat exchange member is formed of a highly thermally conductive material (e.g., at least 50 W/m–K) such as aluminum or aluminum alloy in combination with a zeolite bed in contact with the heat exchange member, and wherein the heat exchange member is shaped and configured so that any given location of the zeolite bed is no more than about 3 inches from the heat exchange member comprising the highly thermally conductive material. Furthermore, the configurations are relatively simple and inexpensive to manufacture and operate. For example, preferred embodiments of the heat exchanger or biogas conditioner may include no moving parts. Various alternative configurations meeting these requirements will be apparent to one of skill in the art in light of the present disclosure, which alternatives fall within the scope of the present invention.

It will also be appreciated that the present claimed invention may be embodied in other specific forms without departing from its spirit or essential characteristics. The described embodiments are to be considered in all respects only as illustrative, not restrictive. The scope of the invention is, therefore, indicated by the appended claims rather than by the foregoing description. All changes that come within the meaning and range of equivalency of the claims are to be embraced within their scope.

What is claimed is:

1. An apparatus for conditioning a biogas stream including biogas and impurities by removing impurities from the biogas stream, the apparatus comprising:
    an upper manifold;
    a lower manifold;
    an inlet through which a biogas stream containing impurities may be introduced into the apparatus;
    an outlet through which a conditioned biogas stream from which impurities have been removed may be removed from the apparatus;
    at least one heat exchange member disposed between the upper and lower manifolds, the heat exchange member comprising a thermally conductive material so as to draw heat away from and/or transfer heat into a zeolite bed or other contents in heat transferring contact with the heat exchange member; and
    a bed comprising zeolite that selectively absorbs impurities from the biogas stream while providing substantially no absorption of the biogas, the zeolite bed being in heat exchanging contact with the heat exchange member, wherein the heat exchange member comprises a thermally conductive material so as to draw heat away from the zeolite bed as the biogas stream containing impurities is introduced through the inlet into the apparatus so as to contact the zeolite bed such that the zeolite adsorbs at least some of the impurities within the biogas stream while absorbing substantially none of the biogas within the biogas stream;
    wherein the at least one heat exchange member is configured so that any given location within the bed is no more than 3 inches from the heat exchange member.

2. An apparatus for conditioning biogas as recited in claim 1, further comprising an outer housing comprising an upper rim and a lower rim;
    wherein the at least one heat exchange member is disposed within the outer housing between the upper rim and the lower rim;
    wherein the zeolite bed is disposed within the outer housing;
    wherein the inlet is disposed through the outer housing or one of the manifolds so as to allow introduction of a biogas stream containing impurities into the outer housing; and
    wherein the outlet is disposed through the outer housing or one of the manifolds so as to allow removal of a conditioned biogas stream from the outer housing.

3. An apparatus for conditioning biogas as recited in claim 2, wherein the heat exchange member comprises a helical fin.

4. An apparatus for conditioning biogas as recited in claim 3, wherein the helical fin is configured so that any given location within the outer housing is no more than 3 inches from the helical fin.

5. An apparatus for conditioning biogas as recited in claim 4, further comprising a heating element thermally coupled to the outer housing, and wherein the helical fin is thermally coupled to the outer housing such that heating of the heating element transfers heat to the outer housing, which transfers heat to the helical fin.

6. An apparatus for conditioning biogas as recited in claim 2, wherein the outer housing comprises an outer tube and the heat exchange member comprises an inner tube that is concentric with the outer tube, the space between the inner tube and the outer tube being no more than 3 inches.

7. An apparatus for conditioning biogas as recited in claim 2, wherein the at least one heat exchange member comprises an inner hollow tube disposed within the outer housing, the inner hollow tube being configured in a helical configuration within the outer housing, the inner hollow tube having a diameter no more than 3 inches.

8. An apparatus for conditioning biogas as recited in claim 1, wherein the at least one heat exchange member comprises a plurality of tubes, each tube extending longitudinally between the upper and lower manifolds, the thickness of each tube being no more than 3 inches, wherein the bed of zeolite is disposed within each tube.

9. An apparatus for conditioning biogas as recited in claim 1, wherein the heat exchange member is configured so that any given location within the packed bed is no more than 1.5 inches from the heat exchange member.

10. An apparatus for conditioning biogas as recited in claim 1, wherein the heat exchange member comprises aluminum.

11. An apparatus for conditioning a biogas stream including biogas and impurities by removing impurities from the biogas stream, the apparatus comprising:
an outer housing, comprising an upper rim and a lower rim;
an inlet through which the biogas stream may be introduced into the outer housing;
at least one heat exchange member disposed within the outer housing and extending between the upper rim and the lower rim;
an outlet through which a conditioned biogas stream from which impurities have been removed may be removed from the outer housing;
a bed comprising zeolite that selectively absorbs the impurities from the biogas stream without absorbing substantially any of the biogas, the zeolite bed being disposed within the outer housing and in heat exchanging contact with the heat exchange member, wherein the heat exchange member comprises a thermally conductive material so as to draw heat away from the zeolite bed as the biogas stream containing impurities is introduced into the outer housing and the zeolite adsorbs at least some of the impurities within the biogas stream without any substantial absorption of the biogas of the biogas stream;
wherein the at least one heat exchange member is configured so that any given location within the zeolite bed is no more than 3 inches from the heat exchange member.

12. A method for conditioning biogas, comprising:
providing at least first and second biogas conditioners, each biogas conditioner being as recited in claim 1;
introducing a biogas stream containing impurities into the first biogas conditioner so as to condition the biogas and provide a conditioned biogas stream from which at least some of the impurities have been removed, the biogas stream containing impurities being introduced into the first biogas conditioner until such time as the bed comprising zeolite within the first biogas conditioner is to be regenerated; and
diverting the biogas stream containing impurities so that it is introduced into the second biogas conditioner rather than the first biogas conditioner such that the biogas is conditioned within the second biogas conditioner while the bed comprising zeolite of the first biogas conditioner is simultaneously regenerated.

13. A method for conditioning biogas as recited in claim 12, wherein the heat exchange member is configured so that any given location within the bed comprising zeolite is no more than 1.5 inches from the heat exchange member.

14. A method for conditioning biogas as recited in claim 13, wherein the heat exchange member comprises aluminum.

15. A method as recited in claim 12, wherein the biogas stream comprises a biogas stream generated from at least one source selected from the group consisting of a confined animal operation, municipal waste, municipal waste water, and a sour natural gas well.

16. A method for conditioning biogas as recited in claim 12, wherein regeneration of the zeolite bed of the first biogas conditioner is achieved by heating the heat exchange member, which transfers heat to the zeolite bed such that impurities adsorbed by the zeolite of the zeolite bed of the first biogas conditioner are released.

17. A method for conditioning biogas as recited in claim 16, wherein each biogas conditioner further comprises a heating element thermally coupled to the heat exchange member, and wherein heating of the heat exchange member is achieved by heating the heating element.

18. A heat-exchanger comprising:
an outer housing including an outer wall and extending between an upper rim to a lower rim;
a helical fin heat exchange-member disposed within the outer housing helixing downward about a longitudinal axis of the outer housing, the fin providing a ramp, a planar projection of which, covers substantially an entire cross-sectional area of the outer housing as the fin ramps downward from a top location near the upper rim of the outer housing to a bottom location near the lower rim, the helical fin heat exchange-member extending substantially continuously from at or near the longitudinal axis laterally outward to at or near the outer wall, the helical fin heat exchange-member extending longitudinally from at or near the upper rim to at or near the lower rim of the outer housing;
wherein the helical fin heat exchange-member comprises a thermally conductive material so as to draw heat away from and/or transfer heat into a zeolite bed or other contents contained within the outer housing and in heat transferring contact with the helical fin heat exchange-member.

19. A heat-exchanger as recited in claim 18, wherein the helical fin heat exchange-member is configured so that any given location within the outer housing is no more than 3 inches from the helical fin heat exchange-member.

20. A heat-exchanger as recited in claim 19, wherein the helical fin heat exchange member comprises aluminum.

* * * * *

UNITED STATES PATENT AND TRADEMARK OFFICE
CERTIFICATE OF CORRECTION

PATENT NO. : 8,414,690 B2  
APPLICATION NO. : 12/859546  
DATED : April 9, 2013  
INVENTOR(S) : Hansen et al.

Page 1 of 1

It is certified that error appears in the above-identified patent and that said Letters Patent is hereby corrected as shown below:

In the Specification

Column 5  
Line 59, change "outer housing" to --interior surface--

Column 6  
Line 42, change "manifold 12" to --manifold 14--

Column 8  
Line 57, change "screen like-material" to --screen-like material--

Column 10  
Line 37, change "conditioner 72" to --conditioner 75--  
Line 43, change "including 37" to --including 37--

Column 13  
Line 23, change "heat exchanges 72" to --heat exchangers 72--  
Line 22, change "includes 37" to --includes 37--

Column 14  
Line 2, change "value added product" to --value-added product--

Signed and Sealed this  
Sixth Day of January, 2015

Michelle K. Lee  
*Deputy Director of the United States Patent and Trademark Office*